United States Patent [19]
Bernáth et al.

[11] Patent Number: 4,605,653
[45] Date of Patent: Aug. 12, 1986

[54] 1-(HYDROXYMETHYL)-1,6,7,11B-TETRAHYDRO-2H,4H-[1,3]OXAZINO- OR -THIAZINO-[4,3-A]ISOQUINOLINE DERIVATIVES AND PHARMACEUTICAL COMPOSITIONS CONTAINING THEM

[75] Inventors: Gábor Bernáth; Jenö Kóbor; Ferenc Fölöp, all of Szeged; Attila Sohajda, Kisvárda; Alajos Kálmán, Budapest; Elemér Ezer, Budapest; György Hajós, Budapest; Éva Pálosi, Budapest; László Dénes, Budapest; László Szporny, Budapest, all of Hungary

[73] Assignee: Richter Gedeon Vegyeszeti Gyar R.T, Budapest, Hungary

[21] Appl. No.: 713,533

[22] Filed: Mar. 19, 1985

[30] Foreign Application Priority Data

Mar. 23, 1984 [HU] Hungary .............................. 1162/84

[51] Int. Cl.[4] ................... A61K 31/535; A61K 31/54; C07D 498/04; C07D 513/04
[52] U.S. Cl. ..................... 514/226; 514/234; 514/237; 514/239; 544/32; 544/89
[58] Field of Search .................... 544/32, 89; 514/226, 514/234, 237, 239

[56] References Cited

U.S. PATENT DOCUMENTS 2,985,649  5/1961  Lombardino et al. ............ 544/32 X
3,157,573 11/1964  Wenner .................................. 514/307

Primary Examiner—Richard L. Raymond
Attorney, Agent, or Firm—Keil & Weinkauf

[57] ABSTRACT

The invention relates to 1-(hydroxymethyl)-1,6,7,11b-tetrahydro-2H,4H-[1,3]oxazino- or -thiazino-[4,3-a]isoquinoline derivatives of the formula (I),

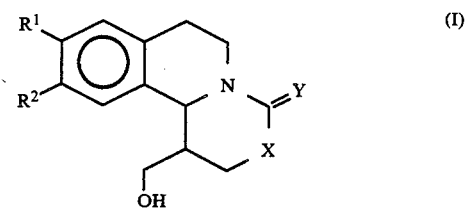

wherein
$R^1$ and $R^2$ are alkoxy having from 1 to 6 carbon atoms,
X is oxygen or sulfur,
Y is =O, =S or an =NR$^3$ group, wherein
$R^3$ is hydrogen, alkyl having from 1 to 6 carbon atoms, cycloalkyl having from 3 to 8 carbon atoms or optionally substituted phenyl,
and acid addition and quaternary salts thereof.

6 Claims, No Drawings

1-(HYDROXYMETHYL)-1,6,7,11B-TETRAHYDRO-2H,4H-[1,3]OXAZINO- OR -THIAZINO-[4,3-A]ISOQUINOLINE DERIVATIVES AND PHARMACEUTICAL COMPOSITIONS CONTAINING THEM

The invention relates to new isoquinoline derivatives, process for their preparation and pharmaceutical compositions containing them as active ingredient. More particularly, the invention concerns new 1-(hydroxymethyl)-1,6,7,11b-tetrahydro-2H,4H-[1,3]oxazino- or -thiazino[4,5-a]isoquinoline derivatives of the formula (I),

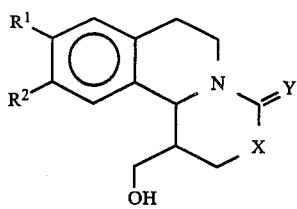

wherein
$R^1$ and $R^2$ represent alkoxy having from 1 to 6 carbon atoms,
X is oxygen or sulfur,
Y is =O, =S, or an =$NR^3$ group, wherein
$R^2$ is hydrogen, alkyl having from 1 to 6 carbon atoms, cycloalkyl having from 3 to 8 carbon atoms or optionally substituted phenyl,
and acid addition and quaternary salts thereof.

The term "alkyl having from 1 to 6 carbon atoms" in the definition of $R^3$ is used to refer to straight-chained or brached alkyl groups, e.g. methyl, ethyl, n-propyl, isopropyl, n-butyl, isobutyl, sec.-butyl, tert.-butyl, n-pentyl, isopentyl, n-hexyl, isohexyl, etc.

The alkoxy groups in the definition of $R^1$ and $R^2$ are straight-chained or branched, and include methoxy, ethoxy, n- or isopropoxy, n-, sec.- or tert.-butoxy, n- or isopentoxy or n- or isohexyloxy, etc.

In the definition of $R^3$ the preferred substituents of phenyl include halogens, preferably chlorine.

A preferred representative of cycloalkyls having from 3 to 8 carbon atoms in the definition of $R^3$ is cyclohexyl.

According to the invention compounds of the formula (I), wherein $R^1$, $R^2$, X, Y and $R^3$ are as defined above, and acid addition and quaternary salts thereof may be prepared by the following processes:

(a) for preparing compounds of the formula (I), in which X is oxygen and Y is an =$NR^3$ group ($R^1$, $R^2$ and $R^3$ are as defined above), ($a_1$) a bis(hydroxymethyl)-methyl isoquinoline derivative of the formula (II),

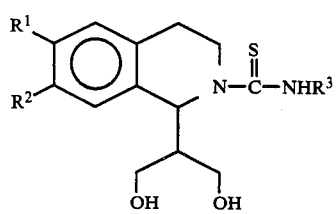

wherein $R^1$, $R^2$ and $R^3$ are as defined above, is reacted with an alkyl halide, and the thiuronium salt obtained is treated with a base, after or without isolation; or ($a_2$) a bis(hydroxymethyl)-methyl-isoquinoline derivative of the formula (III),

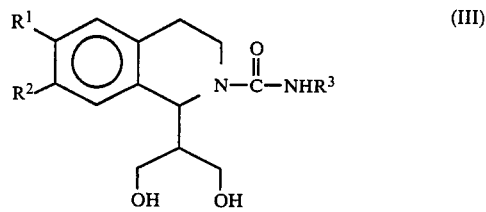

wherein $R^1$, $R^2$ and $R^3$ are as defined above, is treated with a dehydrating agent; or (b) for preparing compounds of the formula (I), in which X is sulfur, Y is an =$NR^3$ group, $R^1$, $R^2$ and $R^3$ are as defined above, a bis(hydroxymethyl)-methyl-isoquinoline derivative of the formula (II), wherein $R^1$, $R^2$ and $R^3$ are as defined above, is treated with an acid; or (c) for preparing compounds of the formula (I), in which X is oxygen, Y is oxygen or sulfur, $R^1$ and $R^2$ are as defined above, a bis(hydroxymethyl)-methyl isoquinoline derivative of the formula (IV),

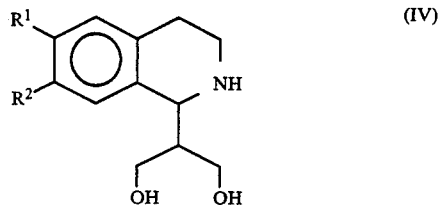

wherein $R^1$ and $R^2$ are as defined above, or an acid addition salt thereof is reacted with a reactive carbonic acid derivative, optionally in the presence of an acid or a base, and, if desired, a compound of the formula (I) obtained, in which Y is oxygen, is converted into a corresponding compound of the formula (I), in which Y is sulfur;

and, if desired, an oxazino-compound prepared according to any of processes ($a_1$), ($a_2$) and (c), in which X is oxygen, Y, $R^1$, $R^2$ and $R^3$ are as defined in the respective process variants, is converted into a corresponding thiazino-compound, in which X is sulfur, while the other substituents are unchanged;

and/or, if desired, a compound of the formula (I), in which Y is sulfur, X, $R^1$ and $R^2$ are as defined above, is converted into a corresponding compound of the formula (I), in which Y is an =$NR^3$ group, $R^3$ is as defined above, while X, $R^1$ and $R^2$ remain unchanged;

and/or, if desired, in a compound of the formula (I), in which Y represents an =$NR^3$ group, X, $R^1$, $R^2$ and $R^3$ are as defined above, the group $R^3$ is replaced by another group within the definition of $R^3$;

and/or, if desired, a compound of the formula (I) is converted into an acid addition or quaternary salt thereof.

The compounds of the formula (I) are pharmaceutically active, for example show vasodilating, antispasm and antidiarrhoeic activity. According to another aspect of the invention there are provided pharmaceutical compositions containing compounds of the formula (I)

of pharmaceutically acceptable salts thereof as active ingredient, in association with pharmaceutical carriers and/or excipients.

The compounds of the formula (I) can structurally be considered cyclic analogues of 3,4-dihydro-2(1H)-isoquinoline carboxamide (U.S. Pat. No. 3,157,573), which is potent hypotensive agent.

The compounds of the formulae (II) and (III) used as starting materials in process variants (a₁), (a₂) and (b) can be prepared from the corresponding N-unsubstituted compounds according to the Hungarian patent application 3652/83 (European patent application No. 84112855.6) by conventional techniques of N-substitution.

The N-unsubstituted compounds of the formula (IV) used as starting materials in process variant (c) are disclosed in the Hungarian patent application 3651/83 (European patent application No. 84112856.4).

In process variant (a₁) preferably methyl iodide is employed as an alkyl halide. The reactant can be used in a molar equivalent amount but preferably the reaction is performed with an excess of the alkyl halide, e.g. methyl iodide. According to a preferred embodiment of process variant (a₁) a compound of the formula (II) is reacted with methyl iodide at room temperature but the reaction may be accomplished also at a slightly elevated temperature. The methylthiuronium iodide formed, after or without isolation, is decomposed with a base, in an organic solvent medium. Parallel with the decomposition of thiuronium salt, ring closure takes place yielding the desired compound of the formula (I). As a base preferably an alkali metal hydroxide or carbonate, most preferably sodium hydroxide or potassium hydroxide, is used, preferably in an alkanolic, e.g. methanolic or ethanolic medium.

According to process variant (a₂) ring closure is performed by treating a compound of the formula (III) with a dehydrating agent. As a dehydrating agent any agent known for this purpose, such as thionyl chloride or phosphorus oxychloride can be used. The reaction rate is satisfactory already at room temperature, therefore there is no need of increasing the temperature.

In process variant (b) preferably mineral acids such as hydrochloric acid, sulfuric acid, phosphoric acid, most preferably hydrochloric acid, is employed as an acid. The reaction is carried out in an inert, preferably polar organic solvent, most preferably an alkanol having from 1 to 4 carbon atoms, e.g. ethanol.

According to process variant (c) the isoquinoline-4-one derivatives of the formula (I) are prepared by reacting compounds of the formula (IV) with reactive carbonic acid derivatives. As reactive carbonic acid derivatives for example phosgene, chloroformic acid methyl or ethyl ester, urea, thiourea, etc. can be used. Depending on the nature of carbonic acid derivatives, the reaction is performed in the presence of a base or an acid. If for example ethyl chloroformate is used, the reaction is carried out in the presence of a base, e.g. an alkali metal bicarbonate such as sodium bicarbonate.

The isoquinoline-4-one compounds obtained in process (c) (Y=oxygen) can be converted into the corresponding isoquinoline-4-thiones (Y=sulfur) by methods known in the art. The conversion is accomplished with a suitable sulfur compound, e.g. phosphorus pentasulfide, in an inert apolar organic solvent, at a temperature between room temperature and the boiling point of the mixture, preferably at elevated temperature.

The oxazine compounds of formula (I), which contains oxygen as X, can be converted into the corresponding thiazino compounds (X=sulfur) in a known manner. The reaction is carried out with a suitable sulfur compound, e.g. phorphorus pentasulfide, in the absence of solvent, by melting a mixture of the starting compound of the formula (I) and phosphorus pentasulfide.

Compounds of the formula (I), in which Y is sulfur, can be converted, if desired, into the corresponding compounds of formula (I), in which Y stands for an =NR³ group. For example, a compound of the formula (I), in which R³ is phenyl, can be prepared by reacting the corresponding isoquinoline-4-thione with aniline, in the presence of Hg(II)oxide. The reaction is carried out in an inert organic solvent, preferably at room temperature.

In the =NR³ group in the definition of Y R³ can be converted, if desired, into another group within the definition of R³. For example compounds in which R³ is phenyl can be obtained by reacting the corresponding compounds, in which R³ represents an alkyl group having from 1 to 4 carbon atoms, preferably ethyl, with aniline. The reaction is performed in an inert organic solvent, preferably alkanol, between room and reflux temperature, preferably under reflux.

The antispasm activity of the compounds was tested by the following methods.

Maximum electroshock (MES) on mice

The shock was applied through a corneal electrode (20 mA, 0.2 msec, HSE Schockgerät typ. 207). The animals which do not show a tonic, extensoric spasm as a result of electroshock treatment are considered protected [see Swinyard et al.: J. Pharmacol. Exp. Ther. 106, 319 (1952)].

Metrazole spasm (MET) on mice

After pretreatment, the animals were administered 125 mg/kg of pentylenetetrazole subcutaneously. The animals which did not show (a) a clonic, (b) a tonic extensoric spasm and which survived the experiment were regarded protected.

Observation time: 1 hour [Everett L. M. and Richards R. K.: J. Pharmacol. Exp. Ther. 81, 402 (1944)].

Test compounds

Compound "A": 1-(hydroxymethyl)-4-(iminophenyl)-9,10-dimethoxy-1,6,7,11b-tetrahydro-2H,4H-[1,3]oxazino[4,3-a]isoquinoline Compound "B": 1-(hydroxymethyl)-4-(iminophenyl)-9,10-diethoxy-1,6,7,11b-tetrahydro-2H,4H-[1,3]thiazino[4,3-a]isoquinoline The results are shown in Table I below.

TABLE I

| Compound | Antispasm activity (%) | |
|---|---|---|
| | MES | MET |
| Compound "A" | — | 40 |
| Compound "B" | — | 40 |

Compounds of the formula (I) according to the invention can be converted into acid addition salts by reaction with suitable acids.

Salt formation can be carried out, for example, in an inert organic solvent, such as an aliphatic alcohol having from 1 to 6 carbon atoms, by dissolving the compound of formula (I) in the solvent and adding the selected acid or a solution thereof formed with the same solvent to the first solution, until it becomes slightly acidic. Thereafter the acid addition salt separates and can be removed from the reaction mixture e.g. by filtration.

The quaternary salts of the compounds of formula (I) are prepared by conventional techniques of quaternization.

If desired, the compounds of the formula (I) or the salts thereof can be subjected to further purification, e.g. recrystallization. The solvents used for recrystallization are selected depending on the solubility and crystallization properties of the compound to be crystallized.

The new compounds of the formula (I) and their physiologically acceptable salts may be formulated for therapeutic purposes. The invention therefore relates also to pharmaceutical compositions; comprising as active ingredient at least one compound of formula (I) or a physiologically acceptable salt thereof, in association with pharmaceutical carriers and/or excipients. Carriers conventional for this purpose and suitable for parenteral or enteral administration as well as other additives may be used. As carriers solid or liquid compounds, for example water, gelatine, lactose, starch, pectin, magnesium stearate, stearic acid, talc, vegetable oils, such as peanut oil, olive oil, arabic gum, polyalkylene glycols, and vaseline (registered trade mark), can be used. The compounds can be formulated as conventional pharmaceutical formulations, for example in solid (globular and angular pills, dragées, capsules, e.g. hard gelatine capsules) or liquid (injectable oil or aqueous solutions or suspensions) form. The quantity of the solid carrier can be varied within wide ranges, but preferably is between 25 mg and 1 g. The compositions optionally contain also conventional pharmaceutical additives, such as preserving agents, wetting agents, salts for adjusting the osmotic pressure, buffers, flavouring agents and aroma substances.

The compositions according to the invention optionally contain the compounds of formula (I) in associated with other known active ingredients. The unit doses are selected depending on the route of administration. The pharmaceutical compositions are prepared by conventional techniques including sieving, mixing, granulation, pressing or dissolution of the active ingredients. The formulations obtained are then subjected to additional conventional treatments, such as sterilization.

The invention is elucidated in detail by the aid of the following non-limiting Examples.

EXAMPLE 1

Preparation of 1-(hydroxymethyl)-4-(iminophenyl)-9,10-dimethoxy-1,6,7,11b-tetrahydro-2H,4H-[1,3]oxazino[4,3-a]isoquinoline Route (A)

To 4.0 g (0.01 mole) of 1-[bis(hydroxymethyl)-methyl]-2-(phenylthiocarboxyamido)-6,7-dimethoxy-1,2,3,4-tetrahydroisoquinoline 4.3 g (0.03 mole) of methyl iodide are added, and the reaction mixture is allowed to stand for 3 to 4 hours. The excess of methyl iodide is evaporated, and the reaction mixture is stirred with 3 moles of abs. methanolic potassium hydroxide until the total amount of methyl mercaptane is eliminated (4 to 6 hours).

The reaction mixture is evaporated to dryness, whereupon a small amount of water is added, and the separated crystalline product is filtered off and washed to neutral with water.

Route (B)

To 4.0 g (0.01 mole) of 1-[bis(hydroxymethyl)-methyl]-2-(phenylthiocarboxamido)-6,7-dimethoxy-1,2,3,4-tetrahydroisoquinoline 4.3 g (0.02 mole) of methyl iodide are added, and the reaction mixture is allowed to stand for 3 to 4 hours. The excess of methyl iodide is evaporated, whereupon the reaction mixture is stirred with 3 moles of abs. methanolic potassium hydroxide until the total elimination of methyl mercaptane (4 to 6 hours). The reaction mixture is evaporated to dryness, and the residue is extracted with five 30-ml portions of hot benzene. The combined benzene phases are evaporated, and the residue is triturated with a small amount of ether to yield the desired compound in crystalline form.

The compounds set forth in Table 1 can be prepared in an analogous manner, by proper selection of the starting substances.

TABLE 1

1-(Hydroxymethyl)-4-(imino-substituted)-9,10-dialkoxy-1,6,7,11b-tetrahydro-2H,4H[1,3]oxazino-[4,3-a]isoquinolines of formula (I) (X = O; Y = =NR$^3$)

| $R^1 = R^2$ | $R^3$ | Formula/ Molecular weight | Melting point (°C.) Solvent | Analysis (%) C | H | N | Yield (%) Route A | B |
|---|---|---|---|---|---|---|---|---|
| CH$_3$O | C$_2$H$_5$ | C$_{17}$H$_{24}$N$_2$O$_4$ 320.38 | 110–112 ethanol | 63.73 63.53 | 7.55 8.00 | 8.75 8.42 | | 63 |
| CH$_3$O | C$_6$H$_5$ | C$_{21}$H$_{24}$N$_2$O$_4$ 368.42 | 202–205 ethanol | 68.46 67.94 | 6.57 6.82 | 7.61 8.02 | 84 | 80 |
| CH$_3$O | C$_6$H$_{11}$ | C$_{21}$H$_{30}$N$_2$O$_4$ 374.47 | 175–178 ethanol | 67.35 67.48 | 8.08 8.27 | 7.48 7.71 | 87 | |
| C$_2$H$_5$O | C$_2$H$_5$ | C$_{19}$H$_{28}$N$_2$O$_4$ 348.43 | 146–148 ethanol | 65.49 65.80 | 8.10 8.25 | 8.04 8.66 | | 73 |
| C$_2$H$_5$O | C$_6$H$_5$ | C$_{23}$H$_{28}$N$_2$O$_4$ 396.47 | 202–203 ethanol | 69.67 69.21 | 7.12 7.31 | 7.07 7.04 | 85 | |
| C$_2$H$_5$O | C$_6$H$_{11}$ | C$_{23}$H$_{34}$N$_2$O$_4$ 402.52 | 185–186 ethanol | 68.62 68.54 | 8.51 8.71 | 6.96 6.90 | 84 | |

EXAMPLE 2

Preparation of
1-(hydroxymethyl)-4-(iminophenyl)-9,10-dimethoxy-
1,6,7,11b-tetrahydro-2H,4H-[1,3]thiazino[4,3-
a]isoquinoline

Route A 4.0 g (0.01 mole) of 1-[bis(hydroxymethyl)-methyl]-2-(phenylthiocarboxamido)-6,7-dimethoxy-1,2,3,4-tetrahydroisoquinoline are refluxed in 20 ml of a solution of hydrochloric acid in absolute ethanol for 15 minutes. The mixture is evaporated to dryness and the residue is taken up in a small amount of water, neutralized with a base and extracted with chloroform. The combined chloroform extracts are dried and evaporated to yield the desired thiazine derivative in crystalline form.

Route B 4.0 g (0.01 mole) of 1-[bis(hydroxymethyl)-methyl]-2-(phenylthiocarboxamido)-6,7-dimethoxy-1,2,3,4-tetrahydroisoquinoline are refluxed for 15 minutes in 20 ml of absolute ethanol containing 25% of dry hydrochloric acid gas. The mixture is evaporated to dryness and, after addition of a small amount of water, neutralized with sodium bicarbonate. The crystalline product is filtered off and washed with water.

The compounds shown in Table 2 are prepared in an analogous manner, by proper selection of the starting substances.

TABLE 2

1-(Hydroxymethyl)-4-(imino-substituted)-9,10-dialkoxy-1,6,7,11b-tetrahydro-2H,4H—[1,3]thiazino[4,3-a]-isoquinolines of the formula (I) (X = S; Y = =NR$^3$)

| $R^1 = R^2$ | $R^3$ | Formula/ Molecular weight | Melting point (°C.) Solvent | Analysis (%) C | H | N | Cl | Yield (%) Route A | B |
|---|---|---|---|---|---|---|---|---|---|
| CH$_3$O | C$_2$H$_5$ | C$_{17}$H$_{24}$N$_2$O$_3$S 336.45 | 164–166 ethanol | 60.68 60.27 | 7.18 7.47 | 8.32 7.94 | | 80 | 70 |
| CH$_3$O | C$_6$H$_5$ | C$_{21}$H$_{24}$N$_2$O$_3$S 384.49 | 188–190 ethanol | 65.60 65.82 | 6.29 6.29 | 7.29 7.35 | | 85 | |
| CH$_3$O | C$_6$H$_{11}$ | C$_{21}$H$_{30}$N$_2$O$_3$S 390.54 | 189–191 ethanol | 64.58 64.08 | 7.74 7.68 | 7.17 7.08 | | 90 | |
| C$_2$H$_5$O | C$_2$H$_5$ | C$_{19}$H$_{28}$N$_2$O$_3$S 364.50 | 141–143 ethanol | 62.60 62.26 | 7.74 7.97 | 7.69 7.70 | | | |
| C$_2$H$_5$O | C$_6$H$_5$ | C$_{23}$H$_{28}$N$_2$O$_3$S 412.54 | 190–191 ethanol | 66.96 67.42 | 6.84 7.14 | 6.79 6.42 | | 83 | |
| C$_2$H$_5$O | C$_6$H$_{11}$ | C$_{23}$H$_{34}$N$_2$O$_3$S 418.59 | 207–209 ethanol | 65.99 65.32 | 8.19 8.04 | 6.69 6.42 | | 85 | |
| CH$_3$O | p-Cl—C$_6$H$_5$ | C$_{21}$H$_{23}$N$_2$O$_3$SCl 455.43 | 210–213 ethanol | 55.33 55.73 | 5.05 5.31 | 6.15 6.17 | 15.57 15.25 | 82 | |
| CH$_3$O | C$_4$H$_9$ | C$_{19}$H$_{28}$N$_2$O$_3$S 364.50 | 149–152 ethanol | 62.60 62.96 | 7.74 8.08 | 7.69 8.10 | | 70 | |

EXAMPLE 3

Preparation of
1-(hydroxymethyl)-4-(iminophenyl)-9,10-dimethoxy-
1,6,7,11b-tetrahydro-2H,4H-[1,3]oxazino[4,3-
a]isoquinoline To 3.9 g (0.01 mole) of 1-[bis(hydroxymethyl)-methyl]-2-phenylcarboxamido-6,7-dimethoxy-1,2,3,4-tetrahydroisoquinoline 10 ml of thionyl chloride are added, whereupon the reaction mixture is allowed to stand overnight. The excess of thionyl chloride is evaporated, the residue is taken up in a small amount of water while cooling, neutralized with sodium bicarbonate and extracted with chloroform. The chloroform phase is dried and evaporated, the residue is crystallized from a mixture of ethanol and ether.

The aimed compound obtained melts at 202° to 205° C. after recrystallization from ethanol. Yield: 17%. The physical and spectroscopical data of the compound obtained are identical with the corresponding parameters of the product obtained in Example 1, and the two products give no melting point depression when admixed.

EXAMPLE 4

Preparation of
1-(hydroxymethyl)-4-(iminophenyl)-9,10-dimethoxy-
1,6,7,11b-tetrahydro-2H,4H-[1,3]thiazino[4,3-
a]isoquinoline 3.68 g (0.01 mole) of 1-(hydroxymethyl)-4-iminophenyl)-9,10-dimethoxy-1,6,7,11b-tetrahydro-2H,4H-[1,3]oxazino[4,3-a]isoquinoline are thoroughly homogenized with 4.4 g (0.02 mole) of phosphorus pentasulfide. The mixture is kept at 150° C. for 2.5 hours. The melt is allowed to cool to room temperature, then it is powdered, 25 ml of a 10% sodium hydroxid solution are added, and the mixture is extracted with water. The ethereal phase is dried, evaporated to dryness and the residue is crystallized from a small amount of a mixture of n-hexane and ether. The desired compound obtained melts at 187° to 190° C. after recrystallization from a mixture of n-hexane and ethanol. Yield: 34%.

The physical and spectroscopical parameters of the compound obtained are identical with the corresponding data of the product prepared according to Example 2, and the two products give no melting point depression when admixed.

EXAMPLE 5

Preparation of
1-(hydroxymethyl)-4-(iminophenyl)-9,10-dimethoxy-
1,6,7,11b-tetrahydro-2H,4H-[1,3]thiazino[4,3-
a]isoquinoline 3.4 g (0.01 mole) of 1-(hydroxymethyl)-4-(iminoethyl)-9,10-dimethoxy-1,6,7,11b-tetrahydro-2H,4H-[1,3]thiazino[4,3-a]isoquinoline are refluxed with 1.86 g (0.02 mole) of aniline in 30 ml of ethanol for 5 hours. The excess of ethanol and aniline is distilled off and crystallized from ethanol to yield the desired compound, melting at 187° to 189° C. Yield: 62%.

The physical data of the compound obtained are identical with those of Example 2, and the two products give no melting point depression when admixed.

EXAMPLE 6

Preparation of 1-[bis(hydroxymethyl)-methyl]-6,7-dimethoxy-1,2,3,4-tetrahydroisoquinoline-N-thiocarboxamide 2.67 g (10.1 mmoles) of 1-[bis(hydroxymethyl)-methyl]-6,7-dimethoxy-1,2,3,4-tetrahydroisoquinoline are suspended in 10 ml of water. To the suspension 1.16 g (0.012 mole) of potassium rhodanide are added, whereupon the reaction mixture is boiled for 6 hours. The substance obtained is cooled, extracted with four 50-ml portions of ethyl acetate, and the combined organic phases are dried over sodium sulfate and evaporated. The oily product is triturated with ether to yield the desired compound in crystalline form. Yield 39%.

Melting point: 146° to 148° C. (ethanol).

| Analysis for $C_{15}H_{22}N_2O_4S$ (326.42): | | | | |
|---|---|---|---|---|
| calculated: | C % = 55.19, | H % = 6.79, | N % = 8.58, | S % = 9.82; |
| found: | C % = 54.91, | H % = 6.69, | N % = 8.23, | S % = 10.30. |

EXAMPLE 7

Preparation of 1-[bis(hydroxymethyl)-methyl]-6,7-diethoxy-1,2,3,4-tetrahydroisoquinoline-N-thiocarboxamide Following the procedure described in Example 6 but starting from the corresponding diethoxyisoquinoline derivative the desired compound is obtained in a yield of 35%.

Melting point: 115° to 117° C. (ethanol).

| Analysis for $C_{17}H_{26}N_2O_4S$ (354.46): | | | | |
|---|---|---|---|---|
| calculated: | C % = 57.60, | H % = 6.82, | N % = 7.90, | S % = 9.05; |
| found: | C % = 57.13, | H % = 6.35, | N % = 7.61, | S % = 9.50 |

EXAMPLE 8

Preparation of 1-(hydroxymethyl)-4-imino-9,10-dimethoxy-1,6,7,11b-tetrahydro-2H-[1,3]oxazino[4,3-a]isoquinoline 3.26 g (0.01 mole) of 1-[bis(hydroxymethyl)-methyl]-6,7-dimethoxy-1,2,3,4-tetrahydroisoquinoline-N-thiocarboxamide prepared according to Example 6 are reacted with 1.42 g (0.1 mole) of methyl iodide. The reaction mixture is allowed to stand at room temperature for 24 hours. The excess of methyl iodide is evaporated and the residue is stirred in 3n methanolic potassium hydroxide for three hours, i.e. until the total elimination of methyl mercaptane. The methanol is then evaporated and the residue is extracted with hot benzene. After evaporation of the solvent the crystalline product obtained is recrystallized from a mixture of diisopropyl ether and ethanol.

Yield: 50%.

Melting point: 124° to 127° C.

| Analysis for $C_{15}H_{20}N_2O_4$ (292.33): | | | |
|---|---|---|---|
| calculated: | C % = 61.63, | H % = 6.89, | N % = 9.58; |
| found: | C % = 62.03, | H % = 6.04, | N % = 8.78. |

EXAMPLE 9

Preparation of 1-(hydroxymethyl)-9,10-dimethoxy-1,6,7,11b-tetrahydro-2H-[1,4]oxazino[4,3-a]-isoquinoline-4-one To 2.67 g (0.01 mole) of 1-[bis(hydroxymethyl)-methyl]-6,7-dimethoxy-1,2,3,4-tetrahydroisoquinoline 0.84 g (0.01 mole) of sodium bicarbonate dissolved in 10 ml of water and 1.08 g (0.01 mole) of chloroformic acid ethyl ester are added, and the mixture obtained is boiled for one hour under stirring. After cooling the reaction mixture is extracted with four 100-ml portions of ether, the combined ethereal phase is dried over sodium sulfate and evaporated to dryness. 0.10 g of sodium methylate are added to the residue and it is heated at 120° C. for 30 minutes. The melt is extracted with four 50-ml portions of hot ethyl acetate and it is then evaporated to 50 ml. Upon cooling needle crystals are precipitated.

Yield: 60%.

Melting point: 125° to 128° C. (ethyl acetate).

| Analysis for $C_{15}H_{19}NO_5$ (293.31): | | | |
|---|---|---|---|
| calculated: | C % = 61.42%, | N % = 6.52, | N % = 4.78; |
| found: | C % = 60.96%, | N % = 6.46, | N % = 6.45. |

EXAMPLE 10

Preparation of 1-(hydroxymethyl)-9,10-diethoxy-1,6,7,11b-tetrahydro-2H-[1,3]oxazino[4,3-a]-isoquinoline-4-one Following the procedure described in Example 9 but starting from the corresponding diethoxy analogue the compound given in the title is obtained.

Yield: 58%.

Melting point: 119° to 121° C. (ethyl acetate).

| Analysis for $C_{17}H_{23}NO_5$ (321.36): | | | |
|---|---|---|---|
| calculated: | C % = 63.53, | H % = 7.21, | N % = 4.36; |
| found: | C % = 63.10, | H % = 7.08, | N % = 4.17. |

EXAMPLE 11

Preparation of 1-(hydroxymethyl)-9,10-dimethoxy-1,6,7,11b-tetrahydro-2H-[1,3]-oxazino-[4,3-a]isoquinoline-4-thione To a solution of 2.67 g (0.01 mole) of 1-[bis(hydroxymethyl)-methyl]-6,7-dimethoxy-1,2,3,4-tetrahydroisoquinoline in 150 ml of absolute chloroform a solution of 2.0 g (0.02 mole) of triethyl amine in 10 ml of absolute chloroform is added, and to the mixture 1.15 g (0.01 mole) of thiophosgene are added dropwise with stirring, under cooling with ice. The reaction mixture is stirred for 10 minutes, then it is washed to neutral with 15 ml of a 5% hydrochloric acid solution and subsequently water. The chloroformic phase is dried over sodium sulfate and evaporated to dryness. The residue is taken up in 15 to 20 ml of ethanol, and ether is added to the mixture until slight turbidity. The desired compound is obtained in crystalline form.

Yield: 19%.

Melting point: 139° to 141° C. (ethanol/ether).

| Analysis for $C_{15}H_{19}NO_4S$ (309.37): | | | | |
|---|---|---|---|---|
| calculated: | C % = 58.23, | H % = 6.19, | N % = 4.53, | S % = 10.36, |
| found: | C % = 57.96, | H % = 6.36, | N % = 4.55, | S % = 10.60. |

EXAMPLE 12

Preparation of 1-(hydroxymethyl)-9,10-dimethoxy-1,6,7,11b-tetrahydro-2H-[1,3]oxazino[4,3-a]-isoquinoline-4-thione 2.93 g (0.01 mole) of 1-hydroxymethyl-9,10-dimethoxy-1,6,7,11b-tetrahydro-2H-[1,3]oxazino[4,3-a]isoquinoline-4-one and 3.33 g (0.015 mole) of phosphorus pentasulfide are boiled in 50 ml of absolute pyridine for two hours. The reaction mixture is cooled and poured onto ice and is extracted with three 50-ml portions of chloroform. The combined organic phases are dried and evaporated to dryness under reduced pressure. The obtained oily residue is passed through a neutral aluminium(III)oxide column. The solution leaving the column is evaporated, and the crystalline residue obtained is recrystallized from a mixture of ethanol and ether.

Yield: 21%.

Melting point: 139° to 141° C.

The characteristics of the crude product obtained are identical with those of the product of Example 11.

EXAMPLE 13

Preparation of 1-(hydroxymethyl)-4-(methylthio)-9,10-dimethoxy-1,6,7,11b-tetrahydro-2H-[1,3]oxazino[4,3-a]isoquinolinium iodide To a solution of 3.09 g (0.01 mole) of 1-(hydroxymethyl)-9,10-dimethoxy-1,6,7,11b-tetrahydro-2H-[1,3]oxazino[4,3-a]isoquinoline-4-thione in acetone 1.94 g (0.02 mole) of methyl iodide are added. The reaction mixture is allowed to stand at room temperature for 24 hours. The crystalline product is filtered off, washed and recrystallized from a mixture of acetone and ether. Yield: 70% (decomposition).

| Analysis for $C_{16}H_{22}INO_4S$ (451.31): | | | |
|---|---|---|---|
| calculated: | C % = 42.58, | H % = 4.69, | N % = 3.10; |
| found: | C % = 43.01, | H % = 4.18, | N % = 2.97. |

EXAMPLE 14

Preparation of 1-(hydroxymethyl)-4-(iminophenyl)-9,10-dimethoxy-1,6,7,11b-tetrahydro-2H-[1,3]oxazino[4,3-a]isoquinoline To a solution of 4.51 g (0.01 mole) of 1-(hydroxymethyl)-2-(methylthio)-9,10-dimethoxy-1,6,7,11b-tetrahydro-2H-[1,3]oxazino[4,3-a]isoquinoline iodide in ethanol 9.3 g (0.10 mole) of aniline are added, and the reaction mixture is boiled for 3 hours. Upon cooling the product separates from the mixture in crystalline form.

Yield: 53%.

Melting point: 201° to 203° C.

The physico-chemical properties of the product obtained are identical with those of the product of Examples 1 and 3, respectively.

EXAMPLE 15

Preparation of 1-(hydroxymethyl)-4-(iminophenyl)-9,10-dimethoxy-1,6,7,11b-tetrahydro-2H-[1,3]oxazino[4,3-a]isoquinoline To a solution of 3.09 g (0.01 mole) of 1-(hydroxymethyl)-9,10-dimethoxy-1,6,7,11b-tetrahydro-2H-[1,3]oxazino[4,3-a]isoquinoline-4-thione in 200 ml of dioxane 0.015 mole of HgO are added, and the mixture is reacted with 9.3 g (0.1 mole) of aniline. The reaction mixture is allowed to stand at room temperature for 24 hours, whereupon the HgS is filtered off, and the solvent and the excess of aniline are distilled off. The aimed compound is obtained in a yield of 45%.

Melting point: 201° to 209° C.

The compound obtained is identical with the products of Examples 1, 3 and 14.

EXAMPLE 16

Preparation of 1-(hydroxymethyl)-4-(iminophenyl)-9,10-dimethoxy-1,6,7,11b-tetrahydro-2H,4H-[1,3]oxazino[4,3-a]isoquinoline Following the procedure of Example 1 the amount of methyl iodide used is reduced to 0.012 mole, using 20 ml of methanol as solvent. The reaction is further performed as described in Example 1. The physical and spectroscopical data of the compound obtained are identical with those of the product prepared according to Example 1.

EXAMPLE 17

Preparation of 1-(hydroxymethyl)-4-(iminomethyl)-9,10-dimethoxy-1,6,7,11b-tetrahydro-2H-[1,3]thiazino[4,3-a]isoquinoline The compound is prepared following the procedure described in Example 1, Route A, starting from 1-[bis(-hydroxymethyl)-methyl]-2-(N'-methyl-thiocarboxamido)-6,7-dimethoxy-1,2,3,4-tetrahydroisoquinoline.

Melting point: 149° to 151° C. (ethanol/ether).

Yield: 65%.

| Analysis for $C_{16}H_{22}NO_3S$ (308.41): | | | |
|---|---|---|---|
| calculated: | C % = 62.31, | H % = 7.29, | N % = 4.54; |
| found: | C % = 62.73, | H % = 7.45, | N % = 4.18. |

EXAMPLE 18

Preparation of 1-(hydroxymethyl)-4-(iminomethyl)-9,10-dimethoxy-1,6,7,11b-tetrahydro-2H-[1,3]thiazino[4,3-a]isoquinoline To a solution of 3.68 g (0.01 mole) of 1-(hydroxymethyl)-4-(iminophenyl)-9,10-dimethoxy-1,6,7,11b-tetrahydro-2H-[1,3]thiazino[4,3-a]isoquinoline in ethanol a 20% solution of 3.1 g (0.1 mole) of methyl amine in methanol is added. The mixture is kept in a sealed tube at 70° C. for three hours, whereupon it is evaporated to dryness under reduced pressure. The oily residue is crystallized by trituration with ether.

Melting point: 149° to 151° C. (ethanol/ether).

Yield: 45%

The physical and spectroscopical data of the product are identical with those of the substance prepared from N'-methyl-thiocarboxamide according to Example 17.

EXAMPLE 19

Preparation of 1-(hydroxymethyl)-4-imino-9,10-dimethoxy-1,6,7,11b-tetrahydro-2H-[1,3]oxazino[4,3-a]isoquinoline This compound is prepared according to Example 1, Route A from 1-[bis(hydroxymethyl)-methyl]-2-thiocarboxamido-6,7-dimethoxy-1,2,3,4-tetrahydroisoquinoline.

Yield: 57%.

Melting point: 125° to 127° C. (ethanol).

| Analysis for $C_{15}H_{20}N_2O_4$ (292.33): | | | |
|---|---|---|---|
| calculated: | C % = 61.63, | H % = 6.89, | N % = 9.58; |
| found: | C % = 61.90, | H % = 6.34, | N % = 9.18. |

We claim:

1. 1-(Hydroxymethyl)-1,6,7,11b-tetrahydro-2H,4H[1,3]oxazino- or -thiazino[4,3-a]isoquinoline derivatives of the formula (I),

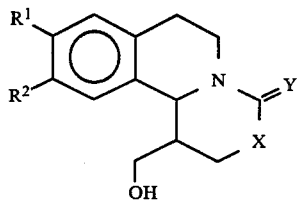

(I)

wherein $R^1$ and $R^2$ are alkoxy having from 1 to 6 carbon atoms,

X is oxygen or sulfur,

Y is =O, =S or an =$NR^3$ group, wherein $R^3$ is hydrogen, alkyl having from 1 to 6 carbon atoms, cycloalkyl having from 3 to 8 carbon atoms, phenyl or halo substituted phenyl, and acid addition and quaternary salts thereof.

2. A compound of the formula I is defined in claim 1, in which $R^1$ and $R^2$ both represent ethoxy or methoxy, and acid addition and quaternary salts thereof.

3. A compound selected from the group consisting of 1-(hydroxymethyl)-4-(iminophenyl)-9,10-dimethoxy-1,6,7,11b-tetrahydro-2H,4H-[1,3]oxazino[4,3-a]isoquinoline and acid addition and quaternary salts thereof, and 1-(hydroxymethyl)-4-(iminophenyl)-9,10-diethoxy-1,6,7,11b-tetrahydro-2H,4H-[1,3]thiazino[4,3-a]isoquinoline and acid addition and quaternary salts thereof.

4. A pharmaceutical composition having vasodilating, antispasm and antidiarrhoeic activity comprising as its active ingredient an effective amount of at least one compound of the formula (I) as defined in claim 1 or pharmaceutically acceptable salts thereof, in association with pharmaceutical carriers and/or excipients.

5. A pharmaceutical composition having vasodilating, antispasm and antidiarrhoeic activity comprising as its active ingredient an effective amount of at least one compound of the formula (I) as defined in claim 2 or pharmaceutically acceptable salts thereof, in association with pharmaceutical carriers and/or excipients.

6. A pharmaceutical composition having vasodilating, antispasm and antidiarrhoeic activity comprising as its active ingredient an effective amount of at least one compound of the formula (I) as defined in claim 3 or pharmaceutically acceptable salts thereof, in association with pharmaceutical carriers and/or excipients.

* * * * *